United States Patent [19]

Gage et al.

[11] Patent Number: 5,919,667
[45] Date of Patent: Jul. 6, 1999

[54] MODULAR ASSEMBLY RETROVIRAL VECTORS AND USES THEREOF

[75] Inventors: Fred H. Gage; Steven T. Suhr, both of La Jolla, Calif.

[73] Assignee: The Salk Institute for Biological Studies, La Jolla, Calif.

[21] Appl. No.: 08/667,025

[22] Filed: Jun. 20, 1996

[51] Int. Cl.⁶ .......................... C12N 15/63; C12N 15/64; C12N 15/67; C12N 15/86

[52] U.S. Cl. .................. 435/91.4; 435/320.1; 435/172.3; 435/69.1; 435/325

[58] Field of Search .............................. 435/172.3, 320.1, 435/325, 69.1, 91.04; 536/23.1, 24.1; 514/44

[56] References Cited

U.S. PATENT DOCUMENTS

| | | | |
|---|---|---|---|
| 4,870,009 | 9/1989 | Evans et al. | 435/69.4 |
| 4,952,496 | 8/1990 | Studier et al. | 435/91.41 |
| 4,981,784 | 1/1991 | Evans et al. | 435/6 |
| 5,071,773 | 12/1991 | Evans et al. | 436/501 |
| 5,171,671 | 12/1992 | Evans et al. | 435/69.1 |

OTHER PUBLICATIONS

Hofman et al., *Prod. Natl. Acad. Sci. USA*, 93: 5185–5190 (1996).
Paulus et al., *Journal of Virology*, 70:62–67 (1996).
Hantzopoulos et al., *Proc. Natl. Acad. Sci. USA*, 86: 3519–3523 (1989).
Yao et al., *Cell Press*, 71: 63–72 (1992).
Wang et al., *Proc. Natl. Acad. Sci. USA*, 91: 8180–8184 (1994).
Gossen et al., *Proc. Natl. Acad. Sci. USA*, 89: 5547–5551 (1992).
Suhr et al., *Arch. Neurol.*, 50: 1252–1268 (1993).
Suhr et al., *Journal of Cellular Biochemistry*, Supplement, 1995, p. 385, Abstract C6–241.
Naldini et al., *Science*, 272: 263–267 (1996).
Li et al., *Journal of Acquired Immune Deficiency Syndromes*, 5: 639–646 (1992).
Terwilliger et al., *Proc. Natl. Acad. Sci. USA*, 86: 3857–3861 (1989).
Orkin, S et al (1995). Report and recommendations of the panel to assin the NIH investment: research in gene therapy.
Mulligan, R. (1993). Science 260, 926–932.
Terwilliger, E. et al (1989). Proc. Natl. Acad. Sci USA 86, 3857–61.
Li, J. et al (1992). Journal of Acquired Immune Deficiency Syndromes 5, 639–46.
Naldini, L. et al (1996). Science 272, 263–67.
Suhr, S. et al (1995). Journal of Cellular Biochemistry Supplement O (21A), 385 (Abstract only).
Suhr, S. et al (1993). Archives of Neurology 50, 1252–68.
Gossen, M. et al (1992). Proc. Natl. Acad. Sci USA 89, 5547–5551.
Wang, Y. et al (1994). Proc. Natl. Acad. Sci 91, 8180–84.
Hantzpoulos, P. et al (1989). Proc. Natl. Acad. Sci 86, 3519–23.

Adam and Miller, "Identification of a Signal in a Murine Retrovirus That Is Sufficient for Packaging of Nonretroviral RNA into Virions" *Journal of Virology*, 62(10) :3802–3806 (1988).
Barklis et al., "Chromosomal Position or Virus Mutation Permits Retrovirus Expression in Embryonal Carcinoma Cells" *Cell*, 47:391–399 (1986).
Cherbas et al., "The Action of Ecdysone in Imaginal Discs and Kc Cells of *Drosophila melanogaster*" *Biosynthesis, Metabolism and Mode of Action of Invertebrate Hormones* (J. Hoffman and M. Porchet, eds.), pp. 305–322; Springer–Verlag, Berlin Heidelberg New York Tokyo (1984).
Harrison, S., "A Structural Taxonomy of DNA–binding Domains" *Nature*, 353:715–719 (1991).
Hofmann et al., "Rapid retroviral delivery of tetracycline–inducible genes in a single autoregulatory cassette" *Proc. Natl. Acad. Sci.*, 93:5185–5190 (1996).
Hoshimaru et al., "Differentiation of the immortalized adult neuronal progenitor cell line HC2S2 into neurons by regulatable supression of the v–myc oncogene" *Proc. Natl. Acad. Sci. USA* 93:1518–1523 (1996).
Jacobs, G., "Determination of the base recognition positions of zinc fingers from sequence analysis" *The EMBO Journal*, 11(12) :4507–4517 (1992).
Jacobs and Michaels, "Zinc Finger Gene Database" *The New Biologist*, 2(6) :583 (1990).
Klug and Rhodes, 'Zinc fingers': a novel protein motif for nucleic acid recognition *Trends in Biochem. Sci.*, 12(6) :464–469 (1987).
Leonard et al., "Charaterization of Somatostatin Transactivating Factor–1, a Novel Homeobox Factor That Stimulates Somatostatin Expression in Pancreatic Islet Cells" *Molecular Endocrinology* 7(10) :1275–1283 (1993).
Miller, A.D., "Retrovirus Packaging Cells" *Human Gene Therapy*, 1:5–14 (1990).
Nakamura and Inouye, "DNA Sequence of the Gene for the Outer Membrane Lipoprotein of *E. coli*: an Extremely AT–Rich Promoter" *Cell* 18:1109–1117 (1979).

(List continued on next page.)

Primary Examiner—Brian R. Stanton
Assistant Examiner—Scott D. Priebe
Attorney, Agent, or Firm—Stephen E. Reiter; Gray Cary Ware & Freidenrich, LLP; Stanley H. Kim

[57] ABSTRACT

In accordance with the present invention, novel retroviral vectors containing modified long terminal repeats (LTRS) which enable high level and ligand-modulatable expression of a desired gene product, even after prolonged periods of cellular quiescence, have been designed and constructed. Invention vectors overcome proviral transcriptional inactivation which occurs in cultured primary cells that are growth arrested due to environmental constraints such as contact inhibition and/or nutrient starvation. Invention vectors represent a class of retroviral vectors in which LTR-promoted proviral expression in infected cells may be maintained or increased, even in situations generally considered to be non-permissive for retroviral vectors.

33 Claims, 5 Drawing Sheets

OTHER PUBLICATIONS

Paulus et al., "Self–Contained, Tetracycline–Regulated Retroviral Vector System for Gene Delivery to Mammalian Cells" *Journal of Virology*, 70(1):62–67 (1996).

Pear et al., "Production of high–titer helper–free retroviruses by transient transfection" *Proc. Natl. Acad. Sci. USA*, 90:8392–8396 (1993).

Rosenberg et al., "Grafting Genetically Modified Cells to the Damaged Brain: Restorative Effects of NGF Expression" *Science* 242:1575–1578 (1988).

Sambrook et al., "Molecular Cloning: A Laboratory Manual" Cold Spring Harbor Press, New York, New York (1989).

Scott et al., "The structure and function of the homeodomain" *Biochem. Biophys. Acta.*, 989:25–48 (1989).

Shimohama et al., "Grafting genetically modified cells into the rat brain: characteristics of *E. coli* β–galactosidase as a reporter gene" *Brain Res. Mol. Brain Res.* 5:271–278 (1989).

Studier et al., "Use of T7 RNA Polymerase to Direct Expression of cloned Genes" *Meth. Enzymol.* 185:60–89, 1990.

Thomas et al., "Heterodimerization of the *Drosophila ecdysone* receptor with retinoid X receptor and *ultraspiracle* " *Nature* 362:471–475 (1993).

Yao et al., "Drosophila untraspiracle Modulates Ecdysone Receptor Function via Heterodimer Formation" *Cell* 71:63–72 (1992).

SEQUENCE LISTING (1) GENERAL INFORMATION:

(iii) NUMBER OF SEQUENCES: 1

(2) INFORMATION FOR SEQ ID NO:1:

```
      (i) SEQUENCE CHARACTERISTICS:
          (A) LENGTH: 71 amino acids
          (B) TYPE: amino acid
          (C) STRANDEDNESS:
          (D) TOPOLOGY: Not Relevant (ii) MOLECULE TYPE: protein (v) FRAGMENT TYPE: internal (xi) SEQUENCE DESCRIPTION: SEQ ID NO:1:

Cys Xaa Xaa Cys Xaa Xaa Asp Xaa Ala Xaa Gly Xaa Tyr Xaa Xaa Xaa
     1               5                   10                  15

Xaa Cys Xaa Xaa Cys Lys Xaa Phe Phe Xaa Arg Xaa Xaa Xaa Xaa Xaa
                     20                  25                  30

Xaa Xaa Xaa Xaa Xaa Cys Xaa Xaa Xaa Xaa Xaa Xaa Xaa Xaa Xaa Cys
                 35                  40                  45

Xaa Xaa Xaa Lys Xaa Xaa Arg Xaa Xaa Cys Xaa Xaa Cys Arg Xaa Xaa
             50                  55                  60

Lys Cys Xaa Xaa Xaa Gly Met
     65                  70
```

MODULAR ASSEMBLY RETROVIRAL VECTORS AND USES THEREOF

ACKNOWLEDGEMENT

This invention was made with Government support under Grant No. AG 10435, awarded by the National Institutes of Health. The Government has certain rights in the invention.

FIELD OF THE INVENTION

The present invention relates to novel retroviral constructs, methods for the preparation thereof, as well as various uses therefor.

BACKGROUND OF THE INVENTION

One of the most pervasive problems in the use of recombinant retroviruses for gene therapy is maintaining transgene expression after cellular infection. In mitotically active cells in culture, such as skin fibroblasts, hepatocytes, or astroglia, retroviruses readily infect and express the integrated transgene. However, when these cells are allowed to reach a post-mitotic state (either in vitro or after transplantation in vivo), expression of the retroviral transcriptional cassette is blocked. Similarly, when retroviral genomes are introduced into embryonic cells, either by normal viral infection or by injection of proviral DNA into the pronucleus, the virus is able to integrate into the host genome, but transgenes introduced in this way are not expressed.

Cells with regulated transgenes have historically been produced by the simultaneous integration of several plasmids into the host cell by transfection. This results in the formation of very few stably transduced cells having all of the required components for regulation intact. Moreover, since variable numbers of plasmids integrate into the host cell genome, individual cells may have very different inductive properties.

To date, no retroviral systems have been described in the art in which transgene expression is regulated through the introduction of novel ligand-activated and/or constitutively active response elements into the LTR thereof. While ligand stimulated transcription systems have been described in plasmids and retroviruses using the tetracycline repressor, these vectors are designed with responsive internal promoters and, therefore, are presumably susceptible to the same LTR transcriptional blockage observed for other retroviral vectors.

Accordingly, what is needed in the art are viruses that have potentially much greater range of application to gene therapy, production of transgenic animals, and gene transfer to developing embryos than previously available retroviral vectors.

BRIEF DESCRIPTION OF THE INVENTION

In accordance with the present invention, we have designed and constructed retroviral vectors having modified long terminal repeats (LTRs) which enable high level and ligand-modulatable expression of a desired gene product, even after prolonged periods of cellular quiescence. Invention vectors overcome proviral transcriptional inactivation which occurs in cultured primary cells that are growth arrested due to environmental constraints such as contact inhibition and/or nutrient starvation. Invention vectors represent a class of retroviral vectors in which LTR-promoted proviral expression in infected cells may be maintained or increased, even in situations generally considered to be non-permissive for retroviral vectors.

As readily recognized by those of skill in the art, there are a variety of areas in which constructs of the present invention can be applied, including:

as gene transfer vectors with the capacity for prolonged transgene expression for either in vivo or ex vivo gene therapy;

as gene transfer vectors with the capacity for modulated transgene expression for either in vivo or ex vivo gene therapy application;

as gene transfer vectors for efficient production of transgenic animals;

as vectors for efficient gene transfer to developing embryos;

as vectors with inducible high titers;

and the like.

BRIEF DESCRIPTION OF THE FIGURES

FIG. 2A–2D present a summary of the inductive properties of native and hybrid EcR, RXRα, and Usp constructs in the presence and absence of an ecdysteroid (e.g., 1 μM muristerone A (MurA)).

FIG. 3A–3C illustrates the ecdysteroid-induced transactivation of native and mutant LTRs containing ecdysteroid response elements.

FIG. 3A presents a schematic representation of the native MLV LTR (designated in the Figure as 3' LTR). The LTR is composed of the U3 region (containing NheI and XbaI sites), the core enhancers, basal transcriptional activation signals, and the R and U5 regions. Native R and U5 regions were left unchanged in these constructs. Transcription is initiated at the U5-R border (depicted with an arrow). Enhancerless constructs were produced by simultaneous digestion of both the XbaI and NheI sites, followed by religation with or without tandem 24-bp EcREs (depicted by an E). Constructs with intact enhancers were digested at either the XbaI or NheI site, and tandem EcREs inserted as shown in the figure.

DETAILED DESCRIPTION OF THE INVENTION

In accordance with the present invention, there are provided constructs comprising:

a retroviral psi (ψ) packaging signal, a 5' long terminal repeat (LTR) and a 3' LTR, wherein one or both of said LTRs comprises an exogenous regulatory element responsive to a transactivator, a transactivator under the expression control of a promoter, a heterologous gene encoding a protein of interest, wherein said heterologous gene is maintained under the control of said regulatory element responsive to said transactivator, and optionally, a selectable marker.

Depending on the application contemplated for the above-described constructs, RNA derived from such constructs can be packaged in infectious virions employing standard techniques, e.g., by passaging such constructs through packaging cell lines, as described, for example, by Miller in *Human Gene Therapy* 1:5–14 (1990).

As readily recognized by those of skill in the art, retroviral psi (ψ) packaging signals useful in the practice of the present invention can be obtained from any of a variety of sources, such as, for example, MLV, HIV, SIV, RSV, MMTV, Foamy virus, and the like. Exemplary psi (ψ) packaging signals contemplated for use herein include ψ-proline, ψ-glutamine, ψ-plus, and the like.

Retroviral long terminal repeats (LTRs) contemplated for use in the practice of the present invention can be obtained from a wide variety of sources. Thus, 5' LTRs and 3' LTRs employed for the preparation of invention constructs can independently be obtained from MLV, HIV, SIV, RSV, MMTV, Foamy virus, and the like.

In accordance with one aspect of the present invention, 5' LTRs and/or 3' LTRs employed for the preparation of invention constructs comprise an exogenous regulatory element responsive to the transactivator present in the construct. One such exogenous regulatory element is an operator which is responsive to a ligand-mediated receptor which confers responsiveness to antibiotics. Exemplary operators contemplated for use in this aspect of the invention include the tetracycline-analog regulated operator, the TET operator, the Lac operator, and the like. Additional operators contemplated for use herein include response elements which are bound by fusion variants of a ligand-mediated member of the steroid/thyroid superfamily of receptors, such as the progesterone/GAL4 fusion transactivator (which binds the GAL4 response element), and the like.

Operators contemplated for use in the practice of the present invention can readily be inserted into any convenient restriction site in either the 5' or 3' LTR. For example, presently preferred sites for insertion of operators into native MLV LTRs are NheI and XbaI.

In accordance with another aspect of the present invention, 5' LTRs and/or 3' LTRs employed for the preparation of invention constructs comprise at least one hormone response element. In a preferred embodiment of this aspect of the invention, the 5' LTRs and/or the 3' LTRs comprise a plurality of hormone response elements.

Hormone response elements contemplated for use in the practice of the present invention can readily be inserted into any convenient restriction site in either the 5' or 3' LTR. For example, presently preferred sites for insertion of hormone response elements into native MLV LTRs are NheI and XbaI.

Hormone response elements contemplated for use herein typically comprise at least two half-sites (in either direct repeat or inverted repeat orientation to one another), separated by a spacer of 0–5 nucleotides. As used herein, the term "half-site" refers to a contiguous 6 nucleotide sequence that is bound by a particular member of the steroid/thyroid superfamily of receptors. Each half-site is typically separated by a spacer of 0 up to about 5 nucleotides. Typically, two half-sites with a corresponding spacer make up a hormone response element. Hormone response elements can be incorporated in multiple copies into various transcription regulatory regions.

Preferred hormone response elements employed in the practice of the present invention comprise a first half-site and a second half-site, separated by a spacer of 0–5 nucleotides;

wherein each half-site has the sequence:

-RGBNNM-, (or complements thereof) wherein each R is independently selected from A or G;

each B is independently selected from G, C, or T;

each N is independently selected from A, T, C, or G; and each M is independently selected from A or C;

with the proviso that at least 4 nucleotides of each -RGBNNM- group of nucleotides are identical with the nucleotides at comparable positions of the sequence -AGGTCA-.

Exemplary half-sites having the -RGBNNM- motif for use in preparing response elements useful in the practice of the present invention include, for example, half-sites selected from -AGGGCA-, -AGTTCA-, -AGGTAA-, -AGGTCA-, -GGTTCA-, -GGGTTA-, -GGGTGA-, -AGGTGA-, -GGGTCA-, and the like. A particularly preferred first half-site is -AGTGCA-.

Ecdysone response elements contemplated for use herein are short cis-acting sequences (i.e., having about 12–20 bp) that are required for activation of transcription in response to a suitable ligand, such as ecdysone or muristerone A, associated with a particular hormone receptor. The native ecdysone response element has been previously described, see, e.g., Yao et al., *Cell,* 71:63–72, 1992. The association of these response elements with otherwise ecdysone-nonresponsive regulatory sequences causes such regulatory sequences to become ecdysone responsive. Ecdysone response element sequences function in a position- and orientation-independent fashion.

In accordance with yet another aspect of the present invention, 5' LTRs and/or 3' LTRs employed for the preparation of invention constructs can be modified by the deletion therefrom of enhancer sequences. Such constructs are particularly useful for expression of heterologous genes where very low background levels are desired in the absence of induction.

Transactivators contemplated for use in the practice of the present invention can be selected from:
- ligand-mediated members of the steroid/thyroid superfamily of receptors, or fusion variants thereof containing at least the ligand binding domain of a member of the superfamily,
- ligand-mediated receptors which confer responsiveness to antibiotics,
- constitutive transactivators,
- and the like.

Ligand-mediated members of the steroid/thyroid superfamily of receptors contemplated for use in the practice of the present invention include hormone binding proteins that operate as ligand-dependent transcription factors, including identified members of the steroid/thyroid superfamily of receptors for which specific ligands have not yet been identified (referred to hereinafter as "orphan receptors").

Exemplary members of the steroid/thyroid superfamily of receptors (including the various isoforms thereof) include steroid receptors such as glucocorticoid receptor (GR), mineralocorticoid receptor (MR), estrogen receptor (ER), progesterone receptor (PR), androgen receptor (AR), vitamin $D_3$ receptor (VDR), and the like; plus retinoid receptors, such as the various isoforms of retinoic acid receptor (e.g., RAR$\alpha$, RAR$\beta$, or RAR$\gamma$), the various isoforms of retinoid X receptor (e.g., RXR$\alpha$, RXR$\beta$, or RXR$\gamma$), and the like (see, e.g., U.S. Pat. Nos. 4,981,784; 5,171,671; and 5,071,773); thyroid receptors (TR), such as TR$\alpha$, TR$\beta$, and the like; insect derived receptors such as the ecdysone receptor, and the like; as well as other gene products which, by their structure and properties, are considered to be members of the superfamily, as defined hereinabove, including the various isoforms thereof.

The DNA-binding domains of all members of the steroid/thyroid superfamily of receptors are related, consisting of 66–68 amino acid residues, and possessing about 20 invariant amino acid residues, including nine cysteines. A member of the superfamily can be characterized as a protein which contains these 20 invariant amino acid residues. The highly conserved amino acids of the DNA-binding domain of members of the superfamily are as follows:

```
Cys-X-X-Cys-X-X-Asp*-X-        (SEQ ID NO:1)
Ala*-X-Gly*-X-Tyr-X-X-
X-X-Cys-X-X-Cys-Lys*-X-
Phe-Phe-X-Arg*-X-X-X-X-
X-X-X-X-(X-X-) Cys-X-
X-X-X-X-(X-X-X-) Cys-X-
X-X-Lys-X-X-Arg-X-X-
Cys-X-X-Cys-Arg*-X-X-
Lys*-Cys-X-X-X-Gly*-Met;
``` wherein X designates non-conserved amino acids within the DNA-binding domain; an asterisk denotes the amino acid residues which are almost universally conserved, but for which variations have been found in some identified hormone receptors; and the residues enclosed in parenthesis are optional residues (thus, the DNA-binding domain is a minimum of 66 amino acids in length, but can contain several additional residues).

A presently preferred receptor contemplated for use herein is the insect-derived ecdysone receptor (as well as fusion variants thereof), since this receptor (as well as ligand and response elements therefor) is not endogenous to mammalian cells contemplated for treatment in accordance with the present invention.

Fusion variants of ligand-mediated members of the steroid/thyroid superfamily of receptors contemplated herein include fusion proteins comprising at least the ligand binding domain of a member of the superfamily and a DNA binding domain capable of binding a response element not endogenous to the LTR. Examples of such fusion proteins are progesterone/GAL4 chimera.

Other transactivators contemplated for use herein include, e.g., homeobox proteins, zinc finger proteins, hormone receptors, helix-turn-helix proteins, helix-loop-helix proteins, basic-Zip proteins (bZip), $\beta$-ribbon factors, and the like. See, for example, Harrison, S., "A Structural Taxonomy of DNA-binding Domains," *Nature*, 353:715–719. Homeobox DNA-binding proteins suitable for use herein include, for example, HOX, STF-1 (Leonard et al., 1993, *Mol. Endo.*, 7:1275–1283), Antp, Mat $\alpha$-2, INV, and the like. See, also, Scott et al. (1989), *Biochem. Biophys. Acta*, 989:25–48. It has been found that a fragment of 76 amino acids (corresponding to amino acids 140–215 described in Leonard et al., 1993, *Mol. Endo.*, 7:1275–1283) containing the STF-1 homeodomain binds DNA as tightly as wild-type STF-1. Suitable zinc finger DNA-binding proteins for use herein include Zif268, GLI, XFin, and the like. See also, Klug and Rhodes (1987), *Trends Biochem. Sci.*, 12:464; Jacobs and Michaels (1990), *New Biol.*, 2:583; and Jacobs (*1992*), *EMBO J.*, 11:4507–4517.

An example of a ligand-mediated receptor which confers responsiveness to antibiotics, as contemplated for use in the practice of the present invention is the tetracycline-controlled transactivator.

Constitutive transactivators contemplated for use in the practice of the present invention include ecdysone receptors containing multiple Vp16 activation domains, Vp16-GAL4 fusions, tetracycline transactivator variants, TTA variants, and the like.

Transactivators contemplated for use in the practice of the present invention may function in the presence or absence of a heterologous partner. Examples of transactivators that typically function in the absence of a heterologous partner are tetracycline-controlled transactivators, steroidogenic factor-1 (SF-1), nerve growth factor-1B (NGF-1B), and the like.

In contrast to the above-described species which function in the absence of a heterologous partner, many members of the steroid/thyroid superfamily of receptors typically function in the presence of heterologous partners therefor, i.e., as multimers. Typically, at least one member of such multimeric species is a member of the steroid/thyroid superfamily. Such multimeric species commonly comprise a member of the steroid/thyroid superfamily, associated with a silent partner therefor. Exemplary silent partners include RXR, Usp, and the like.

Optionally, transactivators and/or multimeric partners therefor can be further modified by the introduction of activation domains thereto. Activation domains contemplated for use herein are typically derived from transcription factors and comprise a contiguous sequence of amino acids that functions to activate gene expression when associated with a suitable DNA-binding domain and a suitable ligand binding domain. The activation domain can be positioned at any convenient site within the transactivator, i.e., at the carboxy terminus, the amino terminus or between the ligand binding domain and the DNA binding domain of the transactivator.

Suitable activation domains can be obtained from a variety of sources, e.g., from the N-terminal region of a member of the steroid/thyroid superfamily of receptors, from a transcription factor activation domain, such as, for example, VP16 or GAL4 activation domains, and the like. The presently most preferred activation domain contemplated for use in the practice of the present invention is obtained from the C-terminal region of the VP16 protein.

Promoters contemplated for control of expression of transactivators employed in the practice of the present invention include inducible, constitutive and/or tissue specific promoters.

Inducible promoters contemplated for use in the practice of the present invention comprise transcription regulatory regions that do not function to transcribe mRNA unless inducing conditions are present. Examples of suitable inducible promoters include DNA sequences corresponding to: the *E. coli* lac operator responsive to IPTG (see Nakamura et al., *Cell,* 18:1109–1117, 1979); the metallothionein promoter metal-regulatory-elements responsive to heavy-metal (e.g. zinc) induction (see Evans et. al, U.S. Pat. No. 4,870, 009), the phage T7lac promoter responsive to IPTG (see Studier et al., *Meth. Enzymol.,* 185: 60–89, 1990; and U.S. Pat. No. 4,952,496), the heat-shock promoter; the TK minimal promoter; the CMV minimal promoter; a synthetic promoter; and the like.

Exemplary constitutive promoters contemplated for use in the practice of the present invention include the CMV promoter, the SV40 promoter, the DHFR promoter, and the like.

Exemplary tissue specific promoters contemplated for use in the practice of the present invention include the GH promoter, the NSE promoter, the GFAP promoter, neurotransmitter promoters (e.g., tyrosine hydroxylase, TH, choline acetyltransferase, ChAT, and the like), promoters for neurotropic factors (e.g., a nerve growth factor promoter, NT-3, BDNF promoters, and the like), and so on.

Heterologous genes contemplated for use in the practice of the present invention include wild type genes and/or a therapeutic genes. Exemplary wild type genes are genes which encode products:

the substantial absence of which leads to the occurrence of a non-normal state in a subject; or a substantial excess of which leads to the occurrence of a non-normal state in a subject.

"Wild type" genes are those that are native to cells of a particular type. Such genes may be undesirably overexpressed, or may not be expressed in biologically significant levels. Thus, for example, while a synthetic or natural gene coding for human insulin would be exogenous genetic material to a yeast cell (since yeast cells do not naturally contain insulin genes), a human insulin gene inserted into a human skin fibroblast cell would be a wild type gene with respect to that cell since human skin fibroblasts contain genetic material encoding human insulin, although human skin fibroblasts do not express human insulin in biologically significant levels.

Therapeutic genes contemplated for use in the practice of the present invention include those which encode products:

which are toxic to the cells in which they are expressed; or which impart a beneficial property to a subject.

As employed hereinrefers to use "therapeutic gene" refers to a gene which imparts a beneficial function to the host in which such gene is expressed. Therapeutic genes are those that are not naturally found in host cells. For example, a synthetic or natural gene coding for wild type human insulin would be therapeutic when inserted into a skin fibroblast cell so as to be expressed in a human host, where the human host is not otherwise capable of expressing functionally active human insulin in biologically significant levels. In accordance with the methods described herein, therapeutic genes are expressed at a level that provides a therapeutically effective amount of the corresponding therapeutic protein.

Numerous genomic and cDNA nucleic acid sequences coding for a variety of proteins are well known in the art. Heterologous genes useful in the practice of the present invention include genes that encode biologically active proteins of interest, such as, e.g., secretory proteins that can be released from said cell; enzymes that can metabolize a toxic substance to produce a non-toxic substance, or that metabolize an inactive substance to produce a useful substance; regulatory proteins; cell surface receptors; and the like. Useful genes include genes that encode blood clotting factors such as human factors VIII and IX; genes that encode hormones such as insulin, parathyroid hormone, luteinizing hormone releasing factor (LHRH), alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor (GM-CSF), colony stimulating factor-1 (CSF-1), tumor necrosis factor (TNF), and erythropoietin (EPO); genes encoding inhibitor substances such as alpha$_1$-antitrypsin; genes encoding substances that function as drugs, e.g., genes encoding the diphtheria and cholera toxins; and the like.

Typically, nucleic acid sequence information for a desired protein can be located in one of many public access databases, e.g., GENBANK, EMBL, Swiss-Prot, and PIR, or in many biology related journal publications. Thus, those of skill in the art have access to nucleic acid sequence information for virtually all known genes. Those of skill in the art can either obtain the corresponding nucleic acid molecule directly from a public depository or the institution that published the sequence. Optionally, once the nucleic acid sequence encoding a desired protein has been ascertained, the skilled artisan can employ routine methods, e.g., polymerase chain reaction (PCR) amplification, to isolate the desired nucleic acid molecule from the appropriate nucleic acid library. Thus, all known nucleic acids encoding proteins of interest are available for use in the methods and products described herein.

Selectable markers contemplated for use in the practice of the present invention include antibiotic resistance genes, genes which enable cells to process metabolic intermediaries, and the like. Exemplary antibiotic resistance genes include genes which impart tetracycline resistance, genes which impart ampicillin resistance, neomycin resistance, hygromycin resistance, puromycin resistance, and the like.

Exemplary genes which enable cells to process metabolic intermediaries include genes which enable cells to incorporate L-histidinol, genes encoding thymidine kinase, genes encoding xanthine-guanine phosphoribosyl transferase (gpt), genes encoding dihydrofolate reductase, genes encoding asparagine synthetase, and the like.

Additional components which can optionally be incorporated into invention constructs include genes encoding those proteins required for retroviral packaging, e.g., the pol gene, the gag gene and the env gene.

Thus, in accordance with the present invention, there is provided a "family" of retroviral vectors, collectively referred to herein as MARVs (for "modular assembly retroviral vectors), which have been designed with LTR promoters that respond to specific constitutive or ligand-dependent transcription factors encoded by nucleic acids which have been introduced into the recombinant retroviral vectors. Three general elements combine to form MARV vectors: 1) native or mutated LTRs containing regulatory elements responsive to a transactivator, wherein said regulatory elements are inserted into various locations within the promoter, 2) transactivator(s), optionally modified to provide a user defined level of expression in the absence of ligand and higher-level expression in the presence of ligand, and 3) retroviral packaging signal, wherein these elements are arranged with endogenous promoters and (optionally) selectable marker genes to result in MARV viruses with other user-definable characteristics.

The first generation of MARV vectors were designed to respond to insect hormones (known as ecdysteroids) to stimulate transcription from the viral LTR. An example of a receptor complex for ecdysteroids is composed of the Drosophila ecdysone receptor (EcR) and the human retinoid X receptor (RXR) or the *Drosophila ultraspiracle* receptor. A hybrid EcR (CofVEcR; see FIG. 2A), in combination with native hRXRα, was extensively tested in the first generation of MARV vectors. This receptor combination results in 20–100-fold transcription induction in the presence of the ecdysteroid muristerone A.

In accordance with the present invention, both single and two plasmid MARV expression systems have been developed. Single-plasmid MARV systems are designed for applications requiring direct in vivo infection where selection is either impossible or impractical.

The two-plasmid system is typically provided with antibiotic resistance markers, which enable the selection and characterization of infected cells in vitro. Thus, in accordance with yet another embodiment of the present invention, there is provided a retroviral vector system, which, when introduced into the genome of a suitable host along with a co-functioning partner therefor, enables ligand-mediated expression of an exogenous protein. One vector of the invention vector system, referred to herein as "MARV", comprises:

a retroviral psi (ψ) packaging signal, a 5' long terminal repeat (LTR) and a 3' LTR, wherein one or both of said LTRs optionally comprises an exogenous regulatory element responsive to a transactivator, a transactivator under the expression control of a promoter, and optionally, a selectable marker, and the other vector of the invention vector system (i.e., the co-functioning partner for the above-described vector) referred to herein as "MARSHA", comprises:

a retroviral psi (ψ) packaging signal, a 5' long terminal repeat (LTR) and a 3' LTR, wherein one or both of said LTRs comprises an exogenous regulatory element responsive to a transactivator, a heterologous gene encoding a protein of interest, wherein said heterologous gene is maintained under the expression control of said regulatory element responsive to said transactivator, and optionally, a selectable marker.

The above-described vectors can be introduced into a suitable host at the same time, or sequentially, employing techniques which are well known in the art. Thus, for example, the vector containing the heterologous gene could be introduced into the host first, followed by the vector encoding the transactivator. Alternatively, the vector encoding the transactivator could be introduced into the host first, followed by the vector containing the heterologous gene.

Thus, in one embodiment, a MARV vector can be designed to encode both subunits of a dimeric receptor and an antibiotic resistance gene (see FIG. 1). A "covector" (referred to herein as MARSHA) is designed to encode the heterologous gene and a second antibiotic resistance gene (see FIG. 1). The MARSHA vector carrying the heterologous gene also has LTRs modified to promote high-level expression only in the presence of the MARV encoded transactivator and exogenous ligand (see FIG. 1). Co-infected primary mammalian cells can then be selected using both antibiotics, resulting in a cell population that is dependent on ligand for high-level expression of the heterologous gene.

By introducing all of the necessary regulatory machinery, plus heterologous genes, selectable markers, and receptors, on the MARV retroviruses, highly efficient insertion of heterologous gene(s) into targeted cells can be achieved. This characteristic of the invention viral system results in individual cells with similar properties resulting in general cell populations with reproducibly characteristic properties of heterologous gene induction. The rapidity and reproducibility of this system makes it useful for ex vivo gene therapy (i.e., for gene transfer to primary cells), particularly in cases where speed is critical to disease treatment.

Thus, the above-described viral constructs address several important problems confronted in the use of retroviruses in application of therapeutic gene transfer strategies to a variety of human diseases. For example, the retroviral vectors of the invention are capable of prolonged gene expression under conditions where conventional integrated retroviruses are no longer transcriptionally active.

In addition to enabling the prolongation of gene expression from integrated proviruses, the present invention allows the level of gene expression to be regulated through the application of exogenous factor(s). In many applications of gene transfer to ameliorate a disease phenotype, only intermittent expression of the therapeutic heterologous gene may be necessary or even desirable. Through the use of different regimens of ligand treatment, the level of heterologous gene expression may be modified. In addition, individual ligand-responsive LTRs have different characteristics of expression which may be included depending on the specific application. For example, the 4X LTR (see FIG. 3A) has a high level of basal expression, which can be increased even further through the application of muristerone A (MurA). Conversely, the 4E LTR (see FIG. 3A) has low basal expression, which can be substantially increased through treatment with hormone. Thus, through the use of LTRs with various properties, the basal and induced expression levels of transgene expression may be "customized".

In accordance with another embodiment of the present invention, there is provided a method of making a modular assembly retroviral vector, said method comprising individually introducing each of the following components into a separate restriction site(s) of DNA engineered to have multiple restriction sites:

a retroviral psi (ψ) packaging signal, a 5' long terminal repeat (LTR) and a 3' LTR, wherein one or both of said LTRs comprises an exogenous regulatory element responsive to a transactivator, a transactivator under the expression control of a promoter, a heterologous gene encoding a protein of interest, wherein said heterologous gene is maintained under the control of a regulatory element responsive to said transactivator, and optionally, a selectable marker.

As readily recognized by those of skill in the art, a variety of additional components can optionally be incorporated into the above-described modular assembly retroviral vectors, such as, for example, genes encoding those proteins required for retroviral packaging, e.g., the pol gene, the gag gene and the env gene.

Thus, it can be seen that invention constructs can be prepared in a very straightforward manner employing a wide variety of readily available starting materials.

In accordance with a further embodiment of the present invention, there are provided modular assembly retroviral vectors prepared as described above, e.g., MARVs comprising DNA engineered to have multiple restriction sites therein, wherein each of the following components is inserted into a separate restriction site(s) thereof:

a retroviral psi (ψ) packaging signal, a 5' long terminal repeat (LTR), and a 3' LTR.

Stated another way, there is provided a modular assembly retroviral vector comprising the following components:

a retroviral psi (ψ) packaging signal, a 5' long terminal repeat (LTR), and a 3' LTR, wherein each component of said vector is bounded by a relatively rare restriction site(s), such that each of said components can be independently removed and/or inserted into separate restriction site(s) on said vector.

The modular assembly retroviral vectors of the invention can not only be prepared in a very straightforward manner employing a wide variety of readily available starting materials, in addition, the design of such vectors renders them amenable to rapid interchange of each of the retroviral components with replacement components from preexisting vectors.

In accordance with a still further embodiment of the present invention, there are provided methods for producing transgenic animals capable of prolonged and regulated expression of heterologous gene(s), said method comprising introducing retroviral construct(s) of the invention, as described hereinabove, into early-stage embryos or stem cells.

As used herein, the phrase "transgenic animal" refers to an animal that contains one or more inheritable expression constructs containing one or more heterologous gene(s) under the transcription control of an operator or hormone response element as described herein. Optionally, an invention transgenic animal also contains one or more inheritable expression constructs containing a member of the steroid/thyroid superfamily of receptors that functions as a silent partner for the active receptor subunit (e.g., RXR).

As employed herein, "introducing" embraces a variety of techniques for contacting target cells with retroviral construct(s) of the invention, such as, for example, by direct injection of such constructs into host cells, by co-injection and/or co-infection of host cells with retroviral construct(s) of the invention, in combination with separate retroviral construct(s) which encode those proteins required for retroviral packaging, by injection and/or infection of host cells with retroviral construct(s) of the invention which themselves contain sequence which encode those proteins required for retroviral packaging, by injection and/or infection with infectious virions prepared from retroviral construct(s) of the invention, and the like.

Methods of making transgenic animals using a particular nucleic acid construct are well-known in the art. When preparing invention transgenic animals, it is preferred that two transgenic lines are generated. The first line will express, for example, RXR and a modified EcR (e.g., VpEcR). Tissue specificity is conferred by the selection of tissue-specific promoters (e.g., T-cell specific) that will then direct the expression of the receptors. A second line contains a regulatory element controlling the expression of an heterologous gene.

In a preferred embodiment of the present invention, an invention transgenic animal contains one or more expression constructs containing nucleic acid encoding an ecdysone receptor, exogenous RXR, and an heterologous gene under the transcription control of an ecdysone response element. It has been found that in transgenic mice containing an ecdysone response element and expressing ecdysone receptor and RXR, muristerone treatment can activate gene expression. Thus, with tissue specific expression of ecdysone receptor and RXR and timely hormone treatment, inducible gene expression can be achieved with spatial, dosage, and temporal specificity.

In accordance with yet another embodiment of the present invention, there are provided in vivo methods for carrying out somatic cell gene therapy, said methods comprising:

introducing retroviral construct of the invention (or both partners of the retroviral vector system of the invention), as described hereinabove, into host tissue, and optionally administering, to said host tissue, ligand for the transactivator.

Ligands contemplated for use herein are compounds which, inside a cell, bind to the transactivator, thereby creating a ligand/receptor complex, which in turn can bind to an appropriate regulatory element.

Preferred ligands contemplated for use in the practice of the present invention are characterized as not normally being present in the cells of the subject, meaning that the ligand is exogenous to the subject. Ecdysteroids, for example, are not naturally present in mammalian systems. Thus, in accordance with the invention method, unless and until an ecdysteroid is administered to the subject, substantially no expression of the desired heterologous gene occurs.

An effective amount of ligand contemplated for use in the practice of the present invention is the amount of ligand (e.g., ecdysteroid) required to achieve the desired level of gene expression product. Ligand can be administered in a variety of ways, as are well-known in the art. For example, such ligands can be administered topically, orally, intravenously, intraperitoneally, intravascularly, and the like.

The terms "ecdysone" and "ecdysteroid" as interchangeably used herein, are employed herein in the generic sense (in accordance with common usage in the art), referring to a family of ligands with the appropriate binding and transactivation activity (see, for example, Cherbas et al., in *Biosynthesis, metabolism and mode of action of invertebrate hormones* (ed. J. Hoffmann and M. Porchet), p. 305–322; Springer-Verlag, Berlin). An ecdysone, therefore, is a compound which acts to modulate gene transcription for a gene maintained under the control of an ecdysone response element.

20-Hydroxy-ecdysone (also known as β-ecdysone) is the major naturally occurring ecdysone. Unsubstituted ecdysone (also known as α-ecdysone) is converted in peripheral tissues to β-ecdysone. Analogs of the naturally occurring ecdysones are also contemplated within the scope of the present invention. Examples of such analogs, commonly referred to as ecdysteroids, include ponasterone A, 26-iodoponasterone A, muristerone A, inokosterone, 26-mesylinokosterone, and the like. Since it has been previously reported that the above-described ecdysones are neither toxic, teratogenic, nor known to affect mammalian physiology, they are ideal candidates for use as inducers in cultured cells and transgenic mammals according to the invention methods.

In accordance with yet another embodiment of the present invention, there are provided ex vivo methods for the treatment of a subject in need of gene therapy, said method comprising introducing the retroviral construct of the invention (or both partners of the retroviral vector system of the invention), as described hereinabove, into cells obtained from said subject, reintroducing the modified cells prepared as described above into said subject, and optionally administering, to said host, ligand for the transactivator.

In accordance with a still further embodiment of the present invention, there are provided methods for extending expression of heterologous gene(s) in retrovirally infected host cells, said method comprising placing said heterologous gene(s) under the expression control of a regulatory element responsive to a transactivator, wherein said cells contain said transactivator.

Heterologous genes contemplated for use in accordance with the present invention include genes encoded by dopaminergic neurons (useful, for example, for the treatment of Parkinson's disease), cholinergic neurons (useful, for example, for the treatment of Alzheimer's disease), hippocampal pyramidal neurons (also useful for the treatment of Alzheimer's disease), norepinephrine neurons (useful, for example, for the treatment of epilepsy), spinal neurons (useful, for example, for the treatment of spinal injury), glutamatergic neurons (useful, for example, for the treatment of schizophrenia), cortical neurons (useful, for example, for the treatment of stroke and brain injury), motor and sensory neurons (useful, for example, for the treatment of amyotrophic lateral sclerosis), and the like.

The invention will now be described in greater detail by reference to the following non-limiting examples.

EXAMPLE 1

MARV was constructed in a modular fashion with individual elements of the recombinant retrovirus inserted sequentially. MARV started as a polylinker composed of 5' NotI-MluI-NruI-EcoRI-AscI-PmlI-BstBI-BamHI -HindIII -HpaI-ClaI-NsiI-KpnI 3' sites. The retroviral ψ gln (see Adam and Miller in J. Virol. 62:3802 (1988) and Barklis et al., in Cell 47:391 (1986)) was inserted SmaI-EcoRI into the NruI-EcoRI sites of the MARV polylinker. The internal CMV promoter was inserted BamHI-ClaI into the BamHI-ClaI sites of the evolving MARV vector. All LTRs destined for insertion into the 5' location were produced by low-cycle/high-fidelity PCR production and end primers with compatible NotI-MluI sites for insertion into the NotI-MluI sites of MARV. 3' LTRs were generated with ClaI-NsiI compatible ends for insertion into these sites. The R region of the 3' LTR was included in the downstream primer sequence. Transgenes, receptor cDNAs, or selectable marker genes were inserted into the remaining polylinker from the EcoRI site through the BamHI site, or the remaining polylinker after the internal promoters (HindIII-ClaI) . By proceeding in this fashion, and taking advantage of the modular design to swap in new modifications, a variety of MARV and MARSHA vectors were constructed, including those schematized in FIG. 1.

The resulting vectors were characterized by restriction digests and mapping, amplified by large-scale plasmid preparation, and prepared for transfection into packaging cells by standard methods. Transient retroviral production in 293 and 293T cells has been previously described (see Pear et al., in Proc Natl Acad Sci USA 90:8392 (1993)). Forty-eight hours after transient retroviral production, the conditioned media was removed, filtered through 0.45 mm filters, and frozen at −70° C. until use. 10-cm dishes of primary-cultured Fisher rat abdominal fibroblasts (Rosenberg et al., Science 242:1575 (1988)) at approximately 50% density were infected with 1/10 volume of virus-containing media and 8 μg polybrene/ml for 48 hours. Infected cells were then selected under the appropriate antibiotic until non-infected cells were cleared from the population (approximately 10 days). Resistant colonies were trypsinized, pooled and passaged. The resulting population was then infected with the second virus, and reselected again in media containing both antibiotics. The infection and selection process for the second round of viral infection proceeded as described for the first round. The final population of doubly resistant primary fibroblasts were then pooled and passaged to 6 or 24-well Costar plates for assay in vitro.

The short (24 hour) course was performed in 24-well Costar dishes with cells at approximately 80% confluency. Five μl of murA (final concentration of 1 μM) or vehicle (20% EtOH) was added to the 1 ml of media in each well. Eight hours after first murA administration, the cells were all washed in PBS and the media was replaced. β-galactosidase histochemical reaction was performed on 1.5% glutaraldehyde-fixed cells essentially as described by Shimohama et al. in Brain Res Mol Brain Res 5:271 (1989) in a 37° C. environment for 2 hours. The 4-day time course was performed in an identical fashion, except that the cell population was plated at only 20% confluency at the start of the experiments (and grew to near-total confluency by the end of the 4 day period) and neither MurA nor media was changed or replaced.

For long-term culture experiments, MMBG fibroblasts were plated in triplicate at high density in 24-well plates. Within 48–72 hours of plating, the cells reached 100% confluency within the wells. At this point, 1 μM murA or vehicle was added to one group of plates, while others were left completely untreated. The wells were then placed in a 37° C.-10% $CO_2$ environment for the next 25 days without any media changes. On day 23, the plates that had received neither vehicle nor murA on day 1 were removed and half of the wells were given vehicle and the other half were given 1 μM murA for 40 hours.

After 25 days of nutrient deprivation and contact inhibition, all of the plates were processed for βgal histochemical staining as above.

MMGH fibroblasts were produced by infection of a MARV-infected fibroblast line with the MARSHA-GH virus. Cells were selected under both antibiotics as described previously. After preliminary examination of murA-induced hGH production in the bulk population, the MMGH population was plated at high density in 6-well Costar plates. Forty-eight hours after the initial plating and when the cells were essentially completely growth inhibited by contact, the medium of all plates was replaced with DME containing 2% FBS. Under these conditions, primary rat fibroblasts stop dividing even if they are not confluent, and settle out into a distended morphology with prominent nuclei characteristic of severely growth-arrested fibroblasts. Six days after acclimatization to this culture environment, 1 ml of medium was harvested from each well and plate of the experiment and stored frozen at −20° C. The remaining unused media was discarded at the same time of harvest and replaced with fresh DME-2% FBS. Groups of wells were treated or not with 1 μM murA. Hormonally treated wells were washed with medium to remove as much residual murA as possible prior to medium replacement when murA treatment was discontinued. This routine was repeated daily for the 21-day extent of the experiment.

After all time-point samples had been collected and frozen at −20° C., they were simultaneously processed for the presence of the hGH protein by ELISA (Boehringer Mannheim) following the protocol recommended by the manufacturer. ELISA data were quantitated on an MR700 microplate reader (Dynatech Laboratories, Chantilly, Va.) and compared to a standard curve generated using purified hGH to determine picogram GH amounts. Control wells were MARV/MARSHA-TH (tyrosine hydroxylase) producing fibroblasts, but displayed all of the MARV/MARSHA characteristics except for the hGH transgene and secreted protein.

EXAMPLE 2

The native MLV LTR was subcloned into a modified version of the cloning vector PBSK for manipulation and mutation of internal sequences. Tandem EcREs were inserted as described with reference to the constructs described in FIG. 2. Mutated LTRs were inserted into a derivative of the pBLluc vector replacing all original TK promoter sequences with the modified LTRs. 100 ng of CofVEcR, 50 ng of CTRL and 100 ng of LTR-reporter and pCH110 internal control were cotransfected, treated and quantified as described with reference to the data presented in FIG. 2.

EXAMPLE 3

EcR, RXRα, and Usp open reading frames (ORFs) were subcloned without internal polyadenylation signals into the cloning vector PBSK (Stratagene, La Jolla, Calif.) for further manipulation of the cDNA sequences. Unique SfiI sites were inserted by PCR mutagenesis into the cDNA sequences of RXRα and Usp overlapping the ATG initiation condon. A similar modification was inserted into the NcoI site approximately 210 bp into the EcR ORF.

C-terminal modification of EcR was performed in an identical fashion except that the inserted SfiI compatible site overlapped the TAG termination condon, recreating it after the site insertion. A plasmid encoding the HSV VP16 τ domain was used as a template for PCR amplification of τ domain sequences with compatible and in-frame ends relative to the inserted SfiI sites in the receptor proteins. All modified receptor proteins were inserted into the vector LNCX (A. D. Miller, GenBank Acc. No. M28247) for expression in transient transfection assays.

Figure 1:
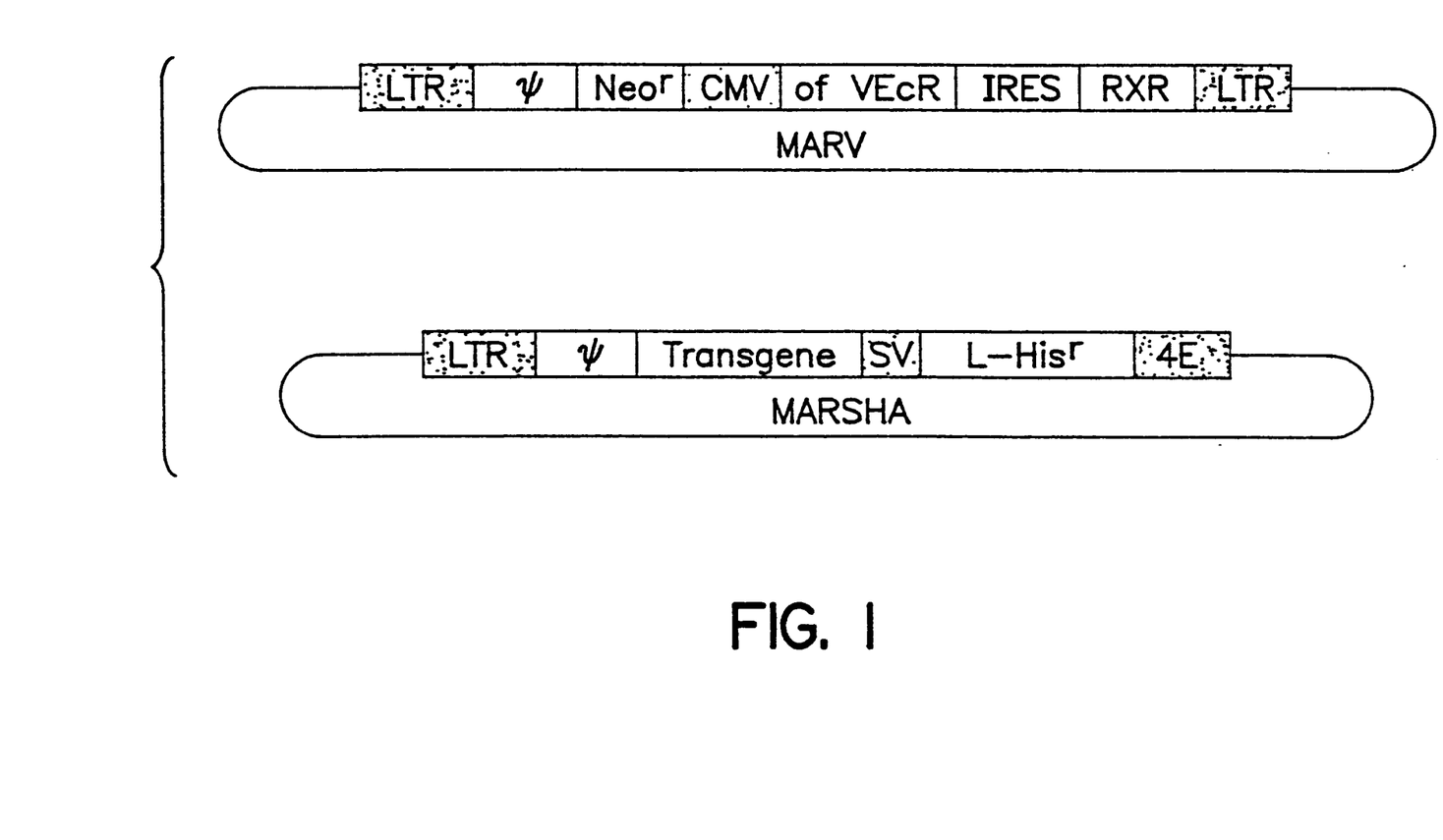
FIG. 1 provides a schematic representation of retroviral vectors according to the invention (designated MARV and MARSHA). In the Figure, "LTR" refers to retroviral long-terminal repeats; "4E" refers to a modified LTR containing ecdysone response elements (EcREs); "ψ" refers to retroviral packaging signals; "Neo$^r$" and "L-His$^r$" refer to antibiotic resistance and metabolic intermediary resistance genes, respectively; "CMV" and "SV" refer to cytomegalovirus and SV40 promoters, respectively; "of VEcR" refers to an EcR mutant receptor with high-level induction and negligible effect on basal activity; "IRES" refers to the internal ribosomal entry site; "RXR" refers to the human RXR alpha open reading frame (ORF); and "Transgene" refers to any gene of interest. In the examples provided herein, the LacZ gene encoding β-galactosidase was used.
Figure 2A:
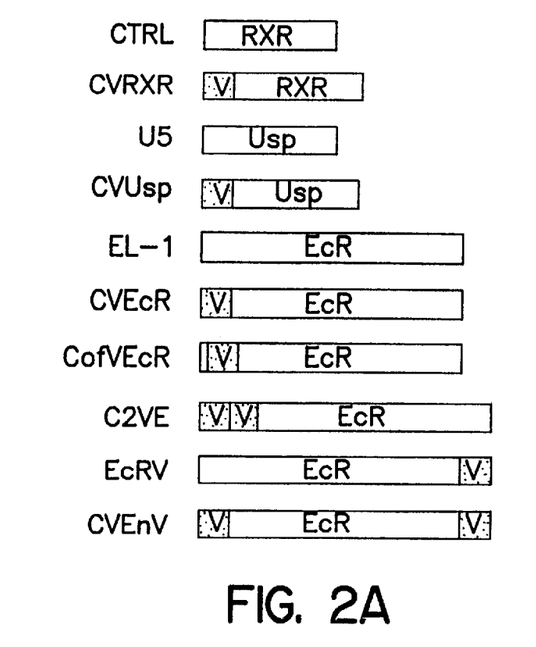
FIG. 2A presents a schematic of the receptors used in transient transfection experiments. "RXRα" refers to the human retinoid X receptor alpha, "EcR" refers to the Drosophila ecdysone receptor, "Usp" refers to the Drosophila ultraspiracle receptor, and "V" refers to the fused 80 amino acid τ domain of HSV VP16.
Figure 2B:
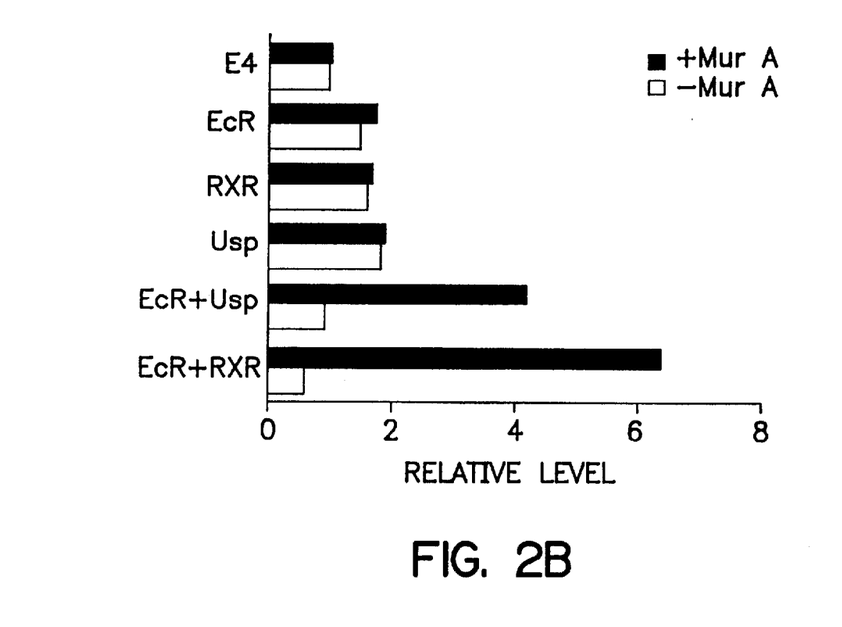
FIG. 2B presents the luciferase activity induced in the presence or absence of MurA, employing native proteins involved in ecdysteroid response (i.e., EcR, RXR, Usp), either alone or in combination.
Figure 2C:
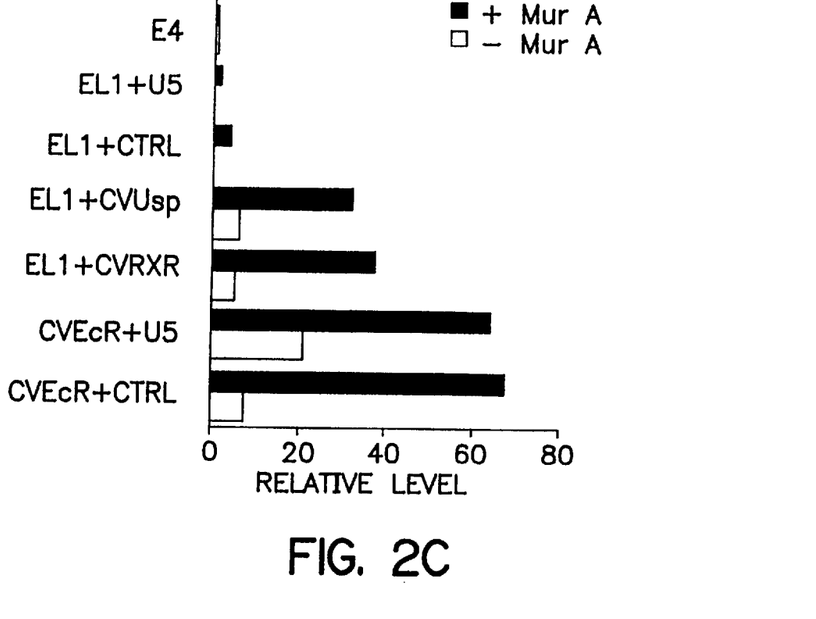
FIG. 2C presents the luciferase activity induced in the presence or absence of MurA, employing either native or hybrid receptor-complex protein combinations, wherein hybrid receptors comprise N-terminal fusions containing the HSV VP16 τ domain (referred to herein as CVRXR, CVUsp, CVEcR, CofVEcR, C2VE, EcRV and CVEnV; see FIG. 2A).
Figure 2D:
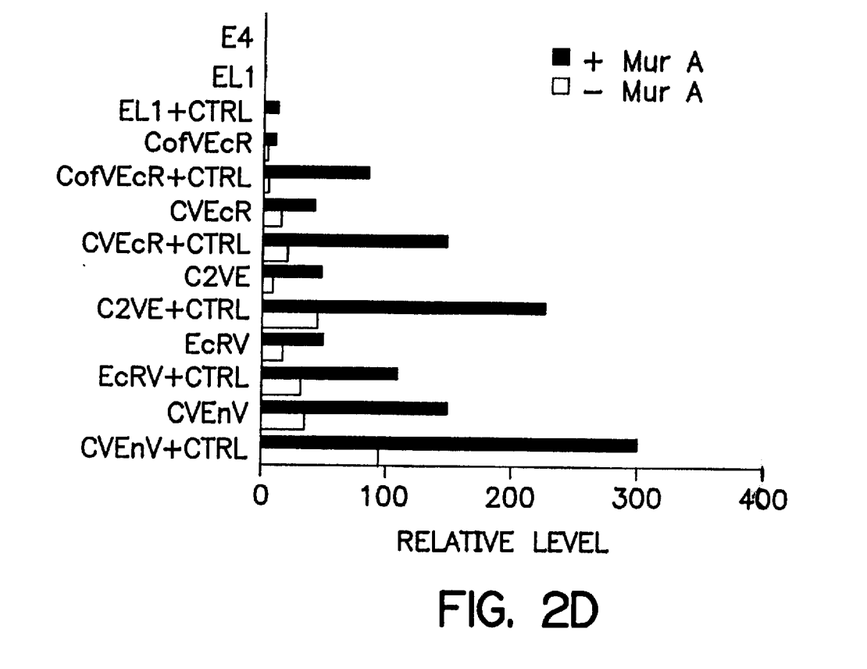
FIG. 2D presents the luciferase activity induced in the presence or absence of MurA, employing EcR hybrids containing the VP16 τ domain, in combination with native hRXRα.
Figure 3A:
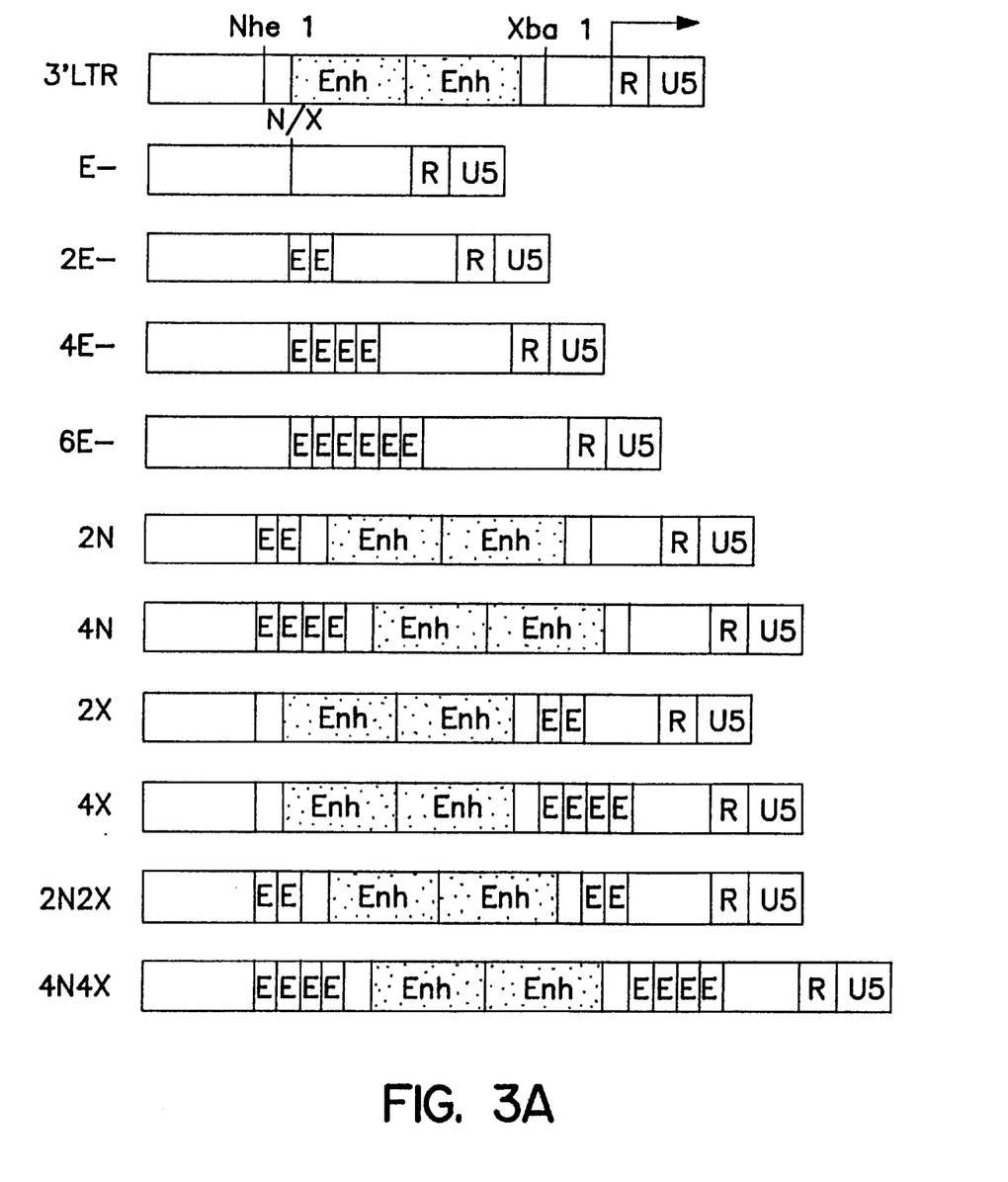
Figure 3B:
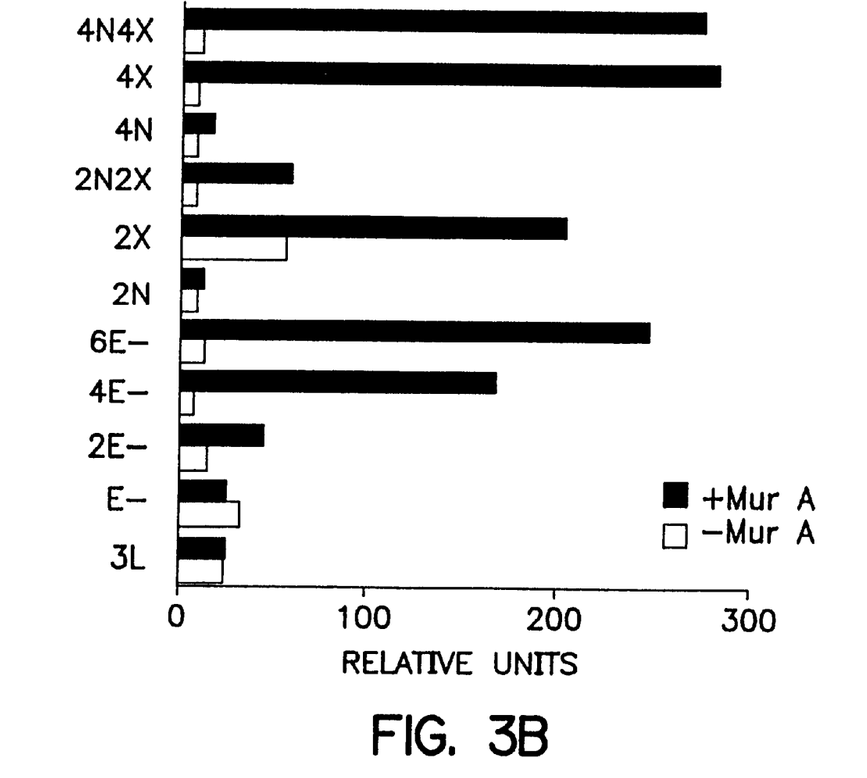
FIG. 3B presents the luciferase activity induced in the presence or absence of 1 μM MurA, employing mutant and native LTR constructs transiently transfected into CV-1 cells.
Figure 3C:
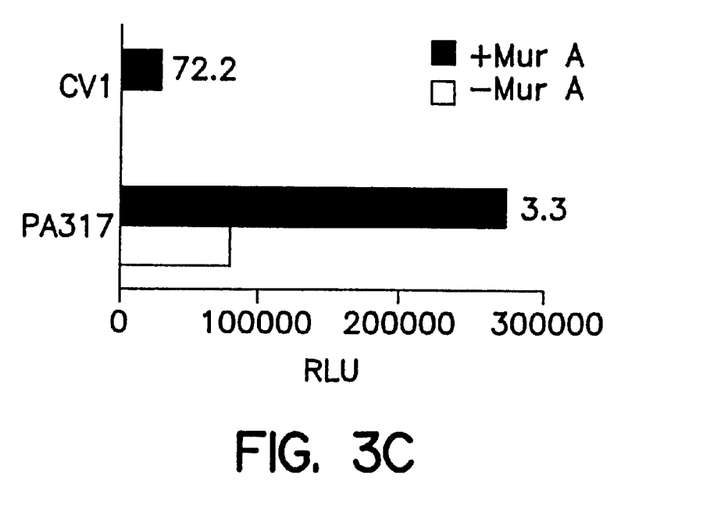
FIG. 3C presents a comparison of the luciferase activity induced by MurA employing the enhancer-containing construct, 4X, in two different cell types, CV-1 and PA317.

The E4luc promoter is 4-tandem EcREs inserted into the BamHI site of plasmid TK-luc which, briefly, is an 180 bp TK minimal promoter with flanking polyadenylation signals to both polyadenylate the 3' end of the nascent luciferase mRNA, and to prevent read-through at the 5' end upstream of the inserted EcREs. The sequences of the EcREs were as described (see Thomas et al., in Nature 362:471 (1993)) with compatible BamHI/BglII, or XbaI/NheI overhangs for insertion into either the pBLluc vector or LTR constructs described in FIG. 3.

Transient transfections were performed by calcium-phosphate coprecipitation employing standard methods (see Sambrook et al., in Molecular Cloning: A Laboratory Manual. Cold Spring Harbor Press, New York, N.Y. (1989)). All tissue culture experiments were performed using DMEM 10% FBS in a 10% $CO_2$ incubator unless otherwise specified. All transfections were performed in triplicate in 24-well Costar plates using CV-1 cells at an approximately $5 \times 10^4$ plating density. Ecdysone receptor plasmid constructs were delivered at 100 ng/well, dimer partner constructs at 50 ng/well, and reporter constructs and internal controls (pCH110) at 100 ng/well for a total of 350 ng DNA/well. Immediately following transfection, 1 μm murA (Sigma, St. Louis, Mo.) (final concentration) in 20% EtOH/PBS was added to wells. After 40 additional hours of incubation, cells were harvested and luciferase activity measured in an analytical bioluminescence photometer. Cell extracts were simultaneously examined for LacZ activity of the internal control by standard methods. Bar graph levels represent relative luciferase activity after correction using internal control values. All molecular biology enzymes and reagents used in this study were proved by either NEB (Beverly, Mass.) or Strategene (La Jolla, Calif.).

EXAMPLE 4

Phase contrast photography was conducted on fields of β-gal stained MARV/MARSHA-βgal coinfected fibroblasts treated with MurA at time 0 and continued for 8 hours with wells stained at 0, 2, 4, 6, 8 and 24 hour intervals. By 6 hours, the first hint of β-gal activity is observed in only one or two cells/field. By 8 hours of treatment, many cells are clearly responding to added hormone. Sixteen hours after hormone is withdrawn (at the 8 hour timepoint, i.e., at 24 hours), the cells have lost the majority of the β-gal activity and have only faint spotty and perinuclear staining.

Bright-field photographs were taken of fields of β-gal stained MARV/MARSHA-βgal coinfected fibroblasts treated with MurA at time 0 and continued for 4 days. Continued treatment of MARV/MARSHA-βgal coinfected fibroblasts with muristerone A is seen to result in higher levels of β-gal activity than transient 8-hour treatments. With extended treatment, cells continue to stain more intensely up to 72-hours, at which time the induction appears to plateau. In addition to more intense staining of individual cells, more cells appear to be recruited into the staining population with hormonal treatments longer than 24 hours, suggesting that most cells in the population have the capability of high-level transgene induction.

Fibroblasts cultured in conditions of contact inhibition with no media changes or other nutrient replenishment for 25 days continue to be strongly positive for β-gal activity as the result of a single treatment with 1 uM MurA on day 1 (note that MurA is not removed as the media is not replenished—this presumably comments on the extended stability of the ecdysteroid in an in vitro situation). Note also that the majority of cells stain for β-gal activity.

Fibroblasts cultured in conditions of contact inhibition with no media changes or other nutrient replenishment for 25 days and then stimulated with 1 uM MurA for the last 40 hours of culture reveals that quiescent, nutrient starved fibroblasts continue to respond strongly to hormone, indicating that the machinery of induction is present at sufficient levels to result in high-level stimulation of transgene expression. Again, most (>80%) of the cells indicate high-level β-gal activity.

EXAMPLE 5

Use of Invention Constructs as a Gene Transfer Vector for Prolonged Transgene Expression for either In Vivo or Ex Vivo Gene Therapy Applications Autologous, explanted skin fibroblasts genetically modified to express tyrosine hydroxylase (TH), the enzyme responsible for synthesis of L-dopa and the precursor for the neurotransmitter dopamine, have proven to ameliorate a loss of local dopamine in animal models of Parkinson's disease. Although quite effective in providing dopamine to the area of neural damage, this technique is only therapeutically useful for 2–3 weeks following transplantation. The decrease in effectiveness has been traced back to a dramatic loss of TH transgene expression in transplanted, post-mitotic cells. The use of invention constructs allows one to overcome the loss of transgene expression by providing stimulation of the retroviral LTR promoter through either ligand-activated transactivating complexes or through constitutive transactivating receptor variants. In this way, transgene expression may be maintained for longer periods of time, even indefinitely if desired.

EXAMPLE 6

Use of Invention Constructs as a Gene Transfer Vector for Modulated Transgene Expression for either In Vivo or Ex Vivo Gene Therapy Application Treatment of Parkinson's disease with the chemical precursor of dopamine, L-dopa, has proven effective in ameliorating many of the deficits of Parkinsonism. With time, however, patients become refractory to L-dopa therapy, with the deleterious effects of chronic treatment outweighing even the serious symptoms of the disease itself. Eventually, patients are left with few therapeutic options. While the transplantation of TH expressing cells may be effective when constantly producing low-levels of L-dopa, a potentially far more beneficial approach would be to allow the physician some degree of control over L-dopa production in the patient. This would allow sufficient control to ensure that the transgenic factor is expressed at appropriate therapeutic levels. At times when endogenous systems are capable of providing full function, the transgene may be allowed to become quiescent and transcriptionally inactive until needed again. Because the transcriptional induction of the invention retroviral constructs is dependent on an exogenous ligand, expression of an integrated therapeutic transgene can be placed under the control of the physician and patient.

EXAMPLE 7

Use of Invention Constructs as a Gene Transfer Vector for Efficient Production of Transgenic Animals Transgenic animals are generally produced by either pronuclear injection of DNA or by transfection of embryonic stem (ES) cells followed by selection and injection of the stem cell into the inner cell mass of very early embryos. Pronuclear injection results in approximately 5–10% stable gene transfer in the production of transgenic mice. The use of ES cells in producing transgenics is likewise inefficient in generating mosaics with germ-line transmission of the transgene. It was proposed in the mid-1980's to use retroviruses to transfer transgenes with high efficiency into early embryos or ES cells to dramatically enhance the odds of producing transgenic animals. All attempts at this failed, not because the virus was incapable of stably integrating into the target cell genome, but because the integrated provirus did not express any of the genes encoded within the viral transcriptional cassette.

The retroviral constructs of the present invention are capable of overcoming the transcriptional block to result in germ-line transgenic animals with full expression from the integrated transgene. In addition to expressing the transgene, the level of transcription may still be regulated by controlling the supply of ligand to the transgenic animal. The increased efficiency of producing transgenic animals by retroviral infection should open up the way to producing mutant animals of a variety of species previously impractical for genetic modification because of the potential cost of producing a large number of non-positive animals by classical methods.

EXAMPLE 8

Use of Invention Constructs as a Vector for Efficient Gene Transfer to Developing Embryos Since retroviral constructs of the present invention can effectively overcome the block of viral expression in embryonic cells, invention constructs are a potent tool in the delivery of transgenes to somatic tissues of a developing embryo. With many diseases, considerable damage is done during embryonic development so that therapies applied after birth are essentially ineffective to ameliorate the disease phenotype.

Retroviral constructs of the present invention can infect cells of the embryo and can provide therapeutic factors to the developing fetus either constitutively, or under the regulation of exogenously produced ligand.

EXAMPLE 9

Use of Invention Constructs as a Vector with Inducible High Titers

One obstacle in the use of retroviruses as gene transfer agents is that titers of retroviruses from existing producer cell lines are only on the order of $1 \times 10^4$ or $1 \times 10^5$. By using a retroviral construct of the invention having intact enhancers and response elements, expression of the retrovirus may be induced by greater than ten-fold, resulting in correspondingly higher titers of infectious virus.

While the invention has been described in detail with reference to certain preferred embodiments thereof, it will be understood that modifications and variations are within the spirit and scope of that which is described and claimed.

That which is claimed is:

1. A retroviral nucleic acid construct comprising;

a retroviral psi (ψ) packaging signal, nucleic acid encoding a transactivator, wherein said transactivator comprises at least the ligand binding domain of a member of the steroid/thyroid superfamily of receptors, and wherein expression of said transactivator is controlled by a promoter, a 5' long terminal repeat (LTR), a 3' LTR, wherein one or both of said LTRs comprises an exogenous regulatory element responsive to said transactivator, and a heterologous gene encoding a protein of interest, wherein said heterologous gene is operably linked to said regulatory element responsive to said transactivator.

2. The construct according to claim 1 wherein said transactivator is:

a ligand-mediated member of the steroid/thyroid superfamily of receptors or a fusion protein comprising at least said ligand binding domain of a member of the superfamily.

3. The construct according to claim 1 wherein said transactivator binds said regulatory element as a multimer.

4. The construct according to claim 3 wherein said multimer is a homomer.

5. The construct according to claim 3 wherein said multimer is a heteromer.

6. The construct according to claim 5 wherein at least one member of said heteromer is RXR or usp.

7. The construct according to claim 1 wherein said 5' long terminal repeat (LTR) or said 3' LTR, or a combination of said 5' and 3' LTRs lack enhancer sequences.

8. The construct according to claim 1 wherein said 5' long terminal repeat (LTR) or said 3' LTR, or a combination of said 5' and 3' LTRs comprises a hormone response element.

9. The construct according to claim 8 wherein said 5' long terminal repeat (LTR) or said 3' LTR, or a combination of said 5' and 3' LTRs comprises a plurality of hormone response elements.

10. The construct according to claim 1 wherein said retroviral psi (ψ) packaging signal is from MLV, HIV, MMTV or Foamy virus.

11. The construct according to claim 1 wherein said promoter is selected from an inducible, a constitutive or a tissue specific promoter, or a combination of any two or more thereof.

12. The construct according to claim 11 wherein said promoter is selected from a TK minimal promoter, a CMV minimal promoter, a CMV promoter, a SV40 promoter, a GH promoter, a NSE promoter, a GFAP promoter, the DHFR promoter, a tyrosine hydroxylase promoter, a choline acetyltransferase promoter, a nerve growth factor promoter or a BDNF promoter.

13. The construct according to claim 1 wherein said heterologous gene is a naturally-occurring gene.

14. The construct according to claim 1 wherein said heterologous gene is toxic to the cells in which they are expressed.

15. The construct according to claim 1, wherein said construct further comprises a selectable marker.

16. The construct according to claim 1 wherein said selectable marker is an antibiotic resistance gene or a gene essential for growth to the cells in which they are expressed.

17. The construct according to claim 1, wherein said nucleic acid is RNA.

18. An infectious virion comprising RNA according to claim 17.

19. A method of making a modular assembly retroviral vector, said method comprising introducing each of the following components into a separate restriction site(s) of DNA engineered to have multiple restriction sites:

a retroviral psi (ψ) packaging signal, nucleic acid encoding a transactivator, wherein said transactivator comprises at least the ligand binding domain of a member of the steroid/thyroid superfamily of receptors and wherein expression of said transactivator is controlled by a promoter, a 5' long terminal repeat (LTR), a 3' LTR, wherein one or both of said LTRs comprises an exogenous regulatory element responsive to said transactivator, a heterologous gene encoding a protein of interest, wherein said heterologous gene is operably linked to said regulatory element responsive to said transactivator.

20. The method according to claim 19 wherein said transactivator is:

a ligand-mediated member of the steroid/thyroid superfamily of receptors or a fusion protein comprising at least said ligand binding domain of a member of the superfamily.

21. The method according to claim 19 wherein said transactivator binds said regulatory element as a multimer.

22. The method according to claim 19 wherein said 5' long terminal repeat (LTR) or said 3' LTR, or a combination of said 5' and 3' LTRs comprises a hormone response element.

23. The method according to claim 22 wherein said 5' long terminal repeat (LTR) or said 3' LTR, or a combination of said 5' and 3' LTRs comprises a plurality of hormone response elements.

24. The method according to claim 19 wherein said retroviral psi (ψ) packaging signal is from MLV, HIV, MMTV or Foamy virus.

25. The method according to claim 20 wherein said promoter is selected from an inducible, a constitutive or a tissue specific promoter, or a combination of any two or more thereof.

26. The method according to claim 20, wherein said construct further comprises a selectable marker.

27. A retroviral vector produced by the method of claim 20.

28. A retroviral vector produced by the method of claim 26.

29. An in vitro method for expressing a heterologous gene in a modified somatic cell, said method comprising:

introducing the construct of claim 1 into a somatic cell, thereby producing said modified cell, subjecting said modified cell to conditions suitable for expression of said construct.

30. The method according to claim 29, wherein said method further comprises administering to said modified cell a ligand for the transactivator.

31. The method according to claim 29, wherein said heterologous gene replaces a gene that is abnormal, deficient or absent from said modified cell.

32. The method according to claim 29, wherein said transactivator is:

a ligand-mediated member of the steroid/thyroid superfamily of receptors, or a fusions protein comprising at least said ligand binding domain of a member of the superfamily.

33. The method according to claim 29, wherein said construct is introduced into a non-proliferating somatic cell.

* * * * *